US012633394B2

(12) United States Patent
Choudhury et al.

(10) Patent No.: US 12,633,394 B2
(45) Date of Patent: May 19, 2026

(54) ACCELERATING TRANSFER AND PROCESSING OF IMAGING INFORMATION WITH DATA PROCESSING UNIT

(71) Applicant: NVIDIA Corporation, Santa Clara, CA (US)

(72) Inventors: Rahul Choudhury, Livermore, CA (US); Chinghsiang Chang, Kirkland, WA (US); Ming Melvin Qin, Mountain View, CA (US)

(73) Assignee: NVIDIA Corporation, Santa Clara, CA (US)

( * ) Notice: Subject to any disclaimer, the term of this patent is extended or adjusted under 35 U.S.C. 154(b) by 486 days.

(21) Appl. No.: 17/860,862

(22) Filed: Jul. 8, 2022

(65) Prior Publication Data
US 2024/0013893 A1     Jan. 11, 2024

(51) Int. Cl.
*G16H 30/20* (2018.01)
*G06T 1/20* (2006.01)
*G16H 30/40* (2018.01)

(52) U.S. Cl.
CPC .............. *G16H 30/20* (2018.01); *G06T 1/20* (2013.01); *G16H 30/40* (2018.01)

(58) Field of Classification Search
CPC ........ G16H 30/20; G16H 30/40; G16H 50/20; G06T 1/20
See application file for complete search history.

(56) References Cited

U.S. PATENT DOCUMENTS

| | | | | |
|---|---|---|---|---|
| 8,203,573 B1* | 6/2012 | Schwarzer | ............... | G09G 5/04 |
| | | | | 345/600 |
| 2002/0184325 A1* | 12/2002 | Killcommons | ......... | G06F 16/10 |
| | | | | 715/733 |
| 2006/0242159 A1* | 10/2006 | Bishop | ................... | G16H 40/67 |
| 2007/0106754 A1* | 5/2007 | Moore | ................... | G16H 40/20 |
| | | | | 707/E17.116 |
| 2007/0147686 A1* | 6/2007 | Joshi | ....................... | G06T 15/08 |
| | | | | 382/232 |
| 2014/0177935 A1* | 6/2014 | Nair | ......................... | A61B 5/33 |
| | | | | 382/132 |
| 2022/0255897 A1* | 8/2022 | Miele | .................. | H04L 63/1425 |
| 2023/0034884 A1* | 2/2023 | Waine | .................. | H04N 19/105 |
| 2023/0035306 A1* | 2/2023 | Liu | ...................... | H04N 19/597 |

OTHER PUBLICATIONS

D. Prateek Shantharama, et al., "Hardware-Accelerated Platforms and Infrastructures for Network Functions: A Survey of Enabling Technologies and Research Studies", IEEE Access, vol. 8, pp. 132021-132085, 2020 (Year: 2020).*

* cited by examiner

*Primary Examiner* — Amber A Misiaszek
(74) *Attorney, Agent, or Firm* — Lowenstein Sandler LLP

(57) ABSTRACT
A system includes a data processing unit (DPU). The DPU is to receive one or more packets for medical imaging data, the one or more packets having a first format that conforms to a medical imaging data protocol. The DPU is to process the one or more packets into one or more updated packets having a second format that does not conform to the medical imaging data protocol and transmit the one or more updated packets to a target device configured to receive packets having the first format that conforms to the medical data protocol.

20 Claims, 11 Drawing Sheets

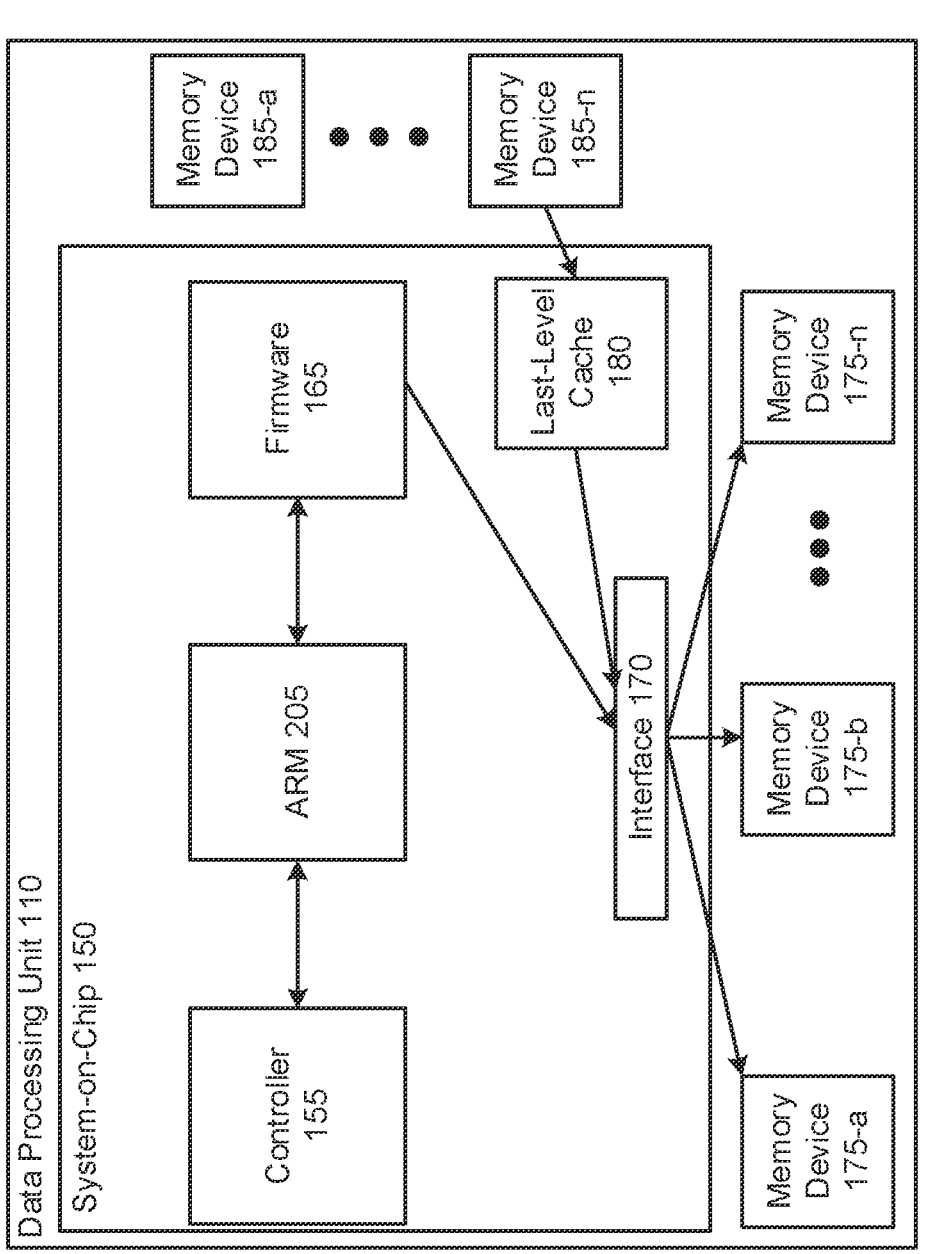
FIG. 1B

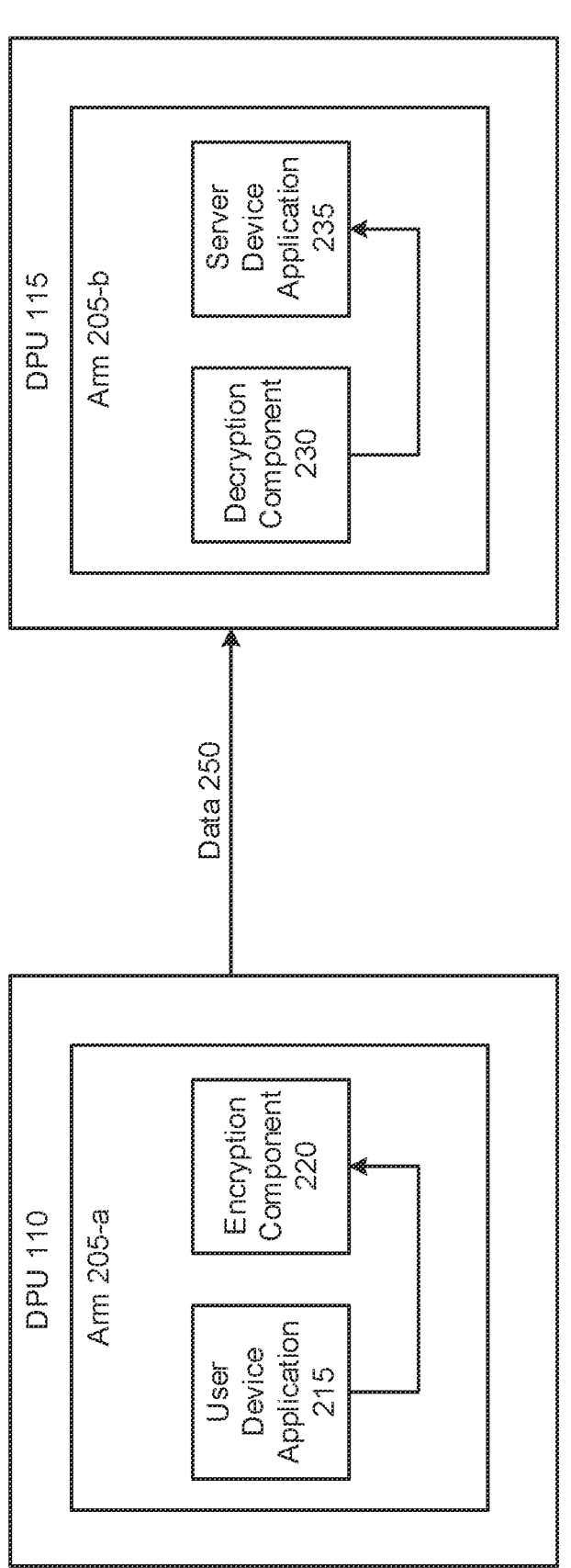
FIG. 2

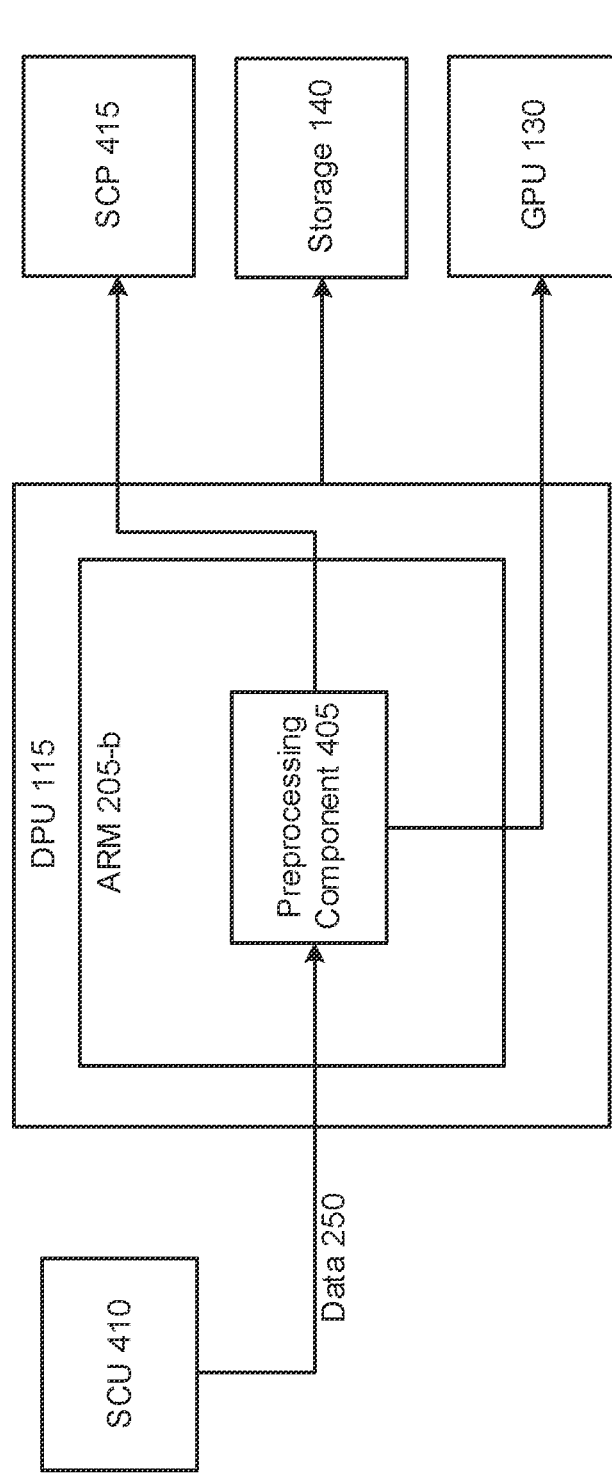
FIG. 4

Picture Archiving and Communication System (PACS) 615

Message 715

Informatics Gateway 610

DPU 110

Data 720

Notification 725

Workflow Manager 705

GPU 130

DPU 115

Data 720

RDMA Read 730

Shared Storage 710

700

800

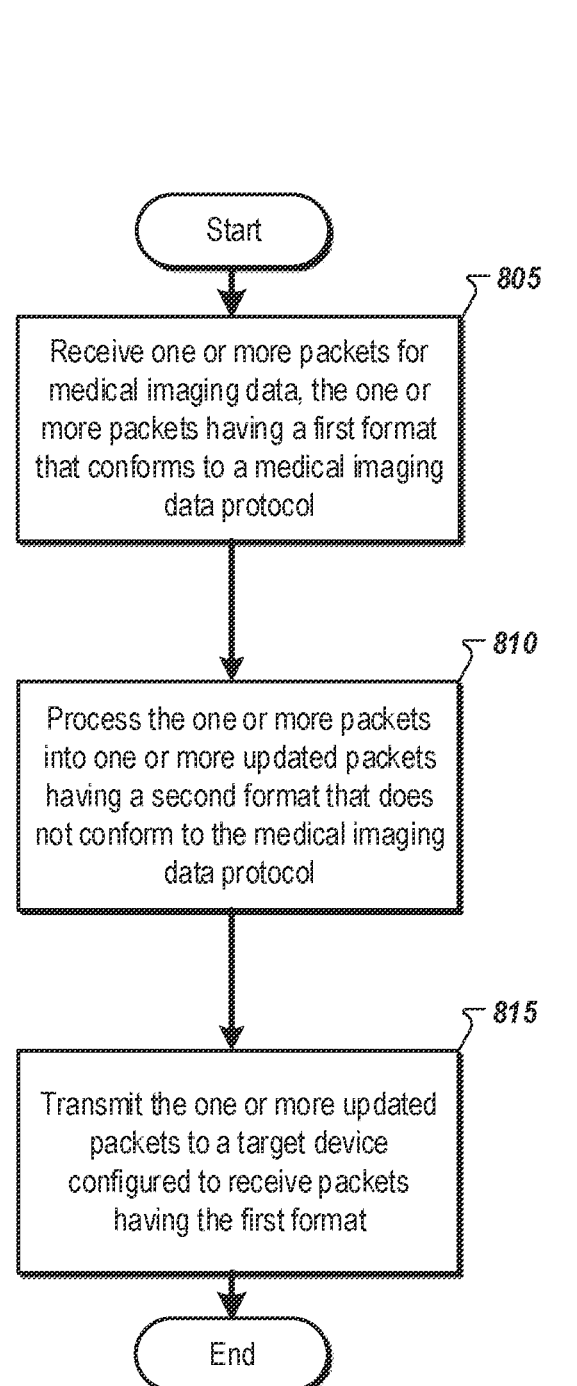

Start

805

Receive one or more packets for medical imaging data, the one or more packets having a first format that conforms to a medical imaging data protocol

810

Process the one or more packets into one or more updated packets having a second format that does not conform to the medical imaging data protocol

815

Transmit the one or more updated packets to a target device configured to receive packets having the first format End

FIG. 8

ACCELERATING TRANSFER AND PROCESSING OF IMAGING INFORMATION WITH DATA PROCESSING UNIT

TECHNICAL FIELD

At least one embodiment pertains to processing resources used to perform and facilitate data transfer and communications. For example, at least one embodiment pertains to technology for accelerating transfer and processing of medical imaging information with data processing units (DPUs).

BACKGROUND

Medical imaging acquisition technology improving has caused a number of images acquired in each imaging study to increase. For example, as magnetic resonance imaging (MRI) and computerized tomography (CT) modalities (e.g., scans) become more efficient at capturing thinner and thinner slices, the number of images acquired increases. This causes healthcare organizations to store petabytes of medical imaging data. Healthcare organizations are also beginning to adopt machine learning and deep learning based algorithms to address clinical diagnosis problems (e.g., process the medical imaging data). Accordingly, it becomes important to have the medical imaging data available to process at an appropriate computation node for the machine learning and other processing performed. Current medical imaging data protocols (e.g., digital imaging and communications in medicine (DICOM)) cause data that is communicated between computation nodes to travel through all open system interconnection (OSI) layers and be accepted and processed by a medical imaging data application. This can increase latencies associated with transmitting and processing the medical imaging data. Additionally, the medical imaging data protocol can be widely adopted making it difficult to change or update. This can cause data encryption or data compression to be slower or outdated.

BRIEF DESCRIPTION OF DRAWINGS

Various embodiments in accordance with the present disclosure will be described with reference to the drawings, in which:

FIG. 1B is an example data processing unit, in accordance with at least some embodiments.

FIG. 2 is an example communication system implementing data processing units (DPUs), in accordance with at least some embodiments;

FIG. 4 is an example communication system implementing data processing units (DPUs), in accordance with at least some embodiments;

FIG. 8 is a flow diagram of a method for accelerating transfer and processing of imaging information using data processing units, in accordance with at least some embodiments.

DETAILED DESCRIPTION

Figure 1A:
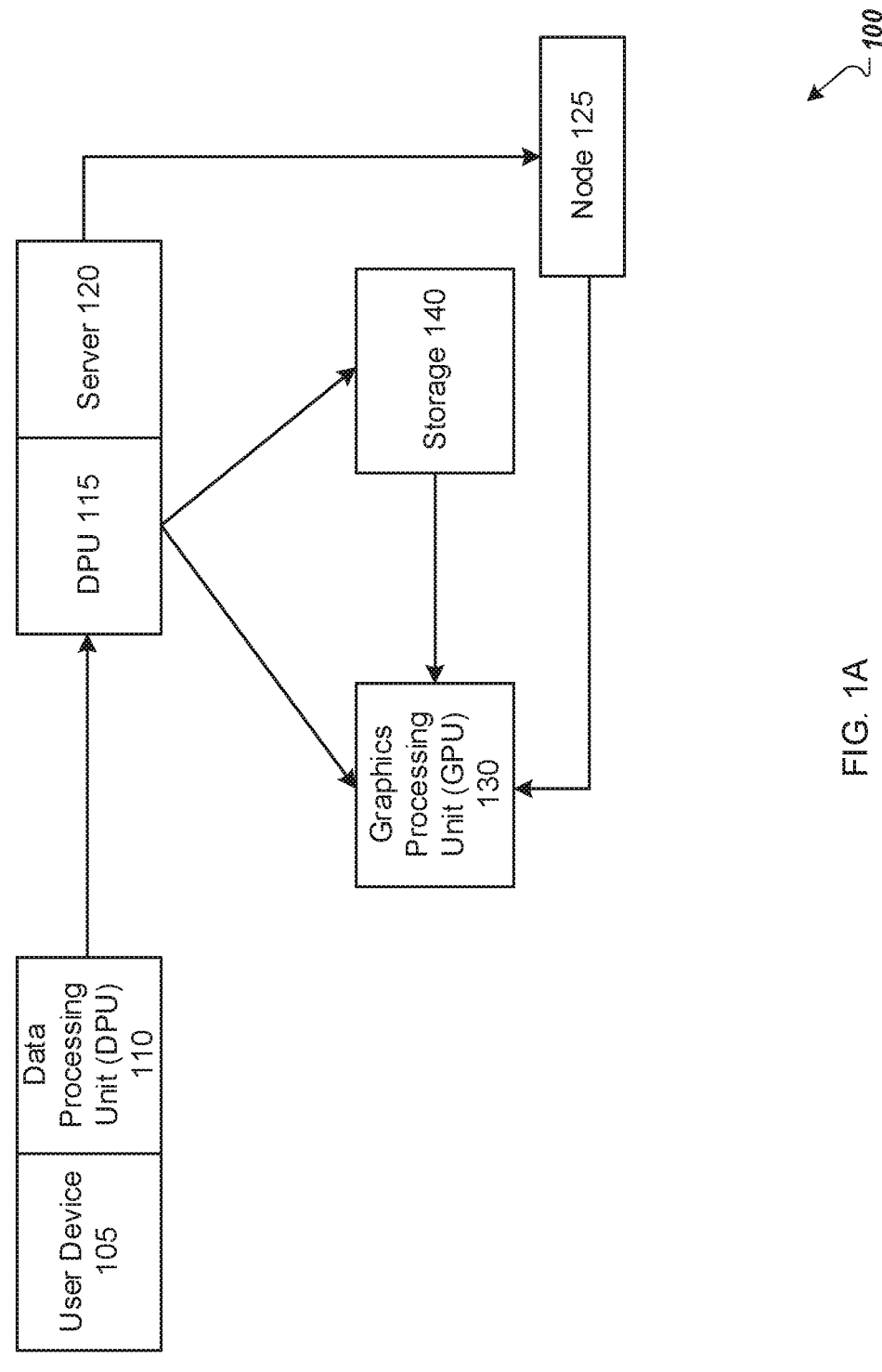
FIG. 1A is an example communication system implementing data processing units (DPUs), in accordance with at least some embodiments.

As medical imaging acquisition technology has advanced and improved, the number of images acquired in each medical imaging study have increased. For example, magnetic resonance imaging (Mill) and computerized tomography (CT) modalities (e.g., scans) have become more efficient at capturing thinner and thinner slices (e.g., images) causing healthcare organizations to store petabytes of information. Medical imaging data (e.g., large medical imaging datasets) are managed by a distributed computing environment and often transmitted and processed according to a medical imaging data protocol. For example, medical imaging data is communicated and processed according to a digital communications in medicine (DICOM) standard that specifies protocols for exchanging medical images and corresponding data.

Healthcare organizations have begun adopting machine learning and deep learning based algorithms to address clinical diagnosis problems—e.g., utilizing machine learning and deep learning based algorithms to process medical imaging data. Medical imaging data can be processed at or input to a machine learning or deep learning model at an appropriate computation node—e.g., to ensure efficient processing, it is important that the medical imaging data is available at the appropriate computation node. Conventional solutions, however, cause medical imaging data communicated by the DICOM protocol to travel through all open systems interconnection (OSI) layers and then be accepted and processed by a DICOM application entity. For example, medical imaging data travels through a kernel layer before reaching either hardware or an application layer. This can increase latencies associated with communicating and processing the medical imaging data. Additionally, many DICOM messages include sensitive medical information about a patient which needs to be kept confidential. However, conventional solutions encrypt or decrypt messages at an application layer executed on a central processing unit (CPU). This can increase latencies and reduce the performance of the CPU. Further, some legacy medical imaging modalities do not have built-in support for transport layer security (TLS), causing communications to be less secure. Further, the DICOM protocol is widely adopted causing difficulties in upgrading or changing the DICOM protocol.

Advantageously, aspects of the present disclosure can address the deficiencies above and other technical problems by utilizing data processing units (DPUs) to accelerate transfer and processing of medical imaging data. For example, a DPU can be coupled to a first device and a second device (e.g., central processing units (CPUs)), where the first device communicates medical imaging data to the second device. In some examples, a DPU can be coupled to a service class user (SCU) (e.g., an application entity executing on the first device) and to a service class provider (SCP)

(e.g. an application entity executing on the second device) that communicate medical imaging data. The DPU coupled to the SCU can encrypt data transmitted and the DPU coupled to the SCP can decrypt data received. This can reduce latencies as compared with performing encryption and decryption in an application layer. The DPU coupled to the SCU can also compress the medical imaging data while the DPU coupled to the SCP can decompress the medical imaging data—e.g., the DPU coupled to the SCU can apply a user defined compression algorithm or determine a compression algorithm to apply based on a type of medical imaging data communicated. These operations can be performed by the DPUs without the knowledge of the SCU and/or SCP, to perform operations such as encryption and/or compression at a lower layer (e.g., at a hardware layer) without modifying the protocol used by the SCP or SCU. Accordingly, DPUs can be leveraged in embodiments to increase security of DICOM data and reduce CPU utilization associated with processing DICOM data.

In some examples, the DPU coupled to the SCP can accelerate the medical imaging communication by performing preprocessing. For example, the DPU coupled to the SCP can extract pixel data and transmit a header (e.g., metadata) to the SCP, reducing latencies. The DPU coupled to the SCP can also communicate the medical imaging data directly to a graphics processing unit (GPU), enabling faster processing. In some examples, the DPU coupled to the SCP can perform filtering by zeroing out pixel data of medical imaging data that is not requested or desired, converting medical imaging data into a tensor, or utilizing a data plane development kit (DPDK). In at least one example, the DPU can accelerate the medical imaging communication by executing a modified SCP—e.g., the DPU can directly execute an instance of the SCP. In such examples, the DPU executing the instance of the SCP can be coupled to a CPU that can perform other operations associated with communicating the medical imaging data. The DPUs coupled to the SCU and/or the SCP can also be utilized to perform remote direct memory access (RDMA) and/or facilitate operations performed by a workflow manager—e.g., a device executing user requests associated with medical imaging data.

By utilizing the DPUs, the overall latency of the system can be reduced. For example, the DPUs can bypass a kernel layer of the system and process information faster than compared with conventional solutions of letting information travel through all layers of the OSI. This can enable faster delivery of medical imaging data, critical in healthcare settings. For example, the DPUs can make data available to relevant computer nodes more efficiently and reduce end-to-end execution time of data processing pipelines. Utilizing DPUs also does not change the DICOM protocol, enabling the system to accelerate data transfer and processing without violating the DICOM protocol. The DPUs can also enable faster copying of large medical imaging data sets from a network layer to a storage layer without relying on transferring the data to a CPU. This can free up CPU resources and reduce latencies for medical imaging machine learning (e.g., artificial intelligence (AI) computation tasks). In some examples, utilizing DPUs can help large scale migration or consolidation of picture archiving and communication systems (PACS) by storing DICOM studies (e.g., a collection of images, presentation states, or SR documents logically related for purpose of diagnosing a patient generated at one or more modalities) directly from a network interface controller (NIC) to storage while transmitting non-pixel metadata to an application entity as described with reference to FIGS. 4 and 5.

Utilizing DPUs can also improve compression and encryption of medical imaging data. The encryption, decryption, compression, and decompression can take place in hardware instead of at an application layer which decreases latencies. By processing information faster, the DPUs can also provide information more efficiently to computational nodes, machine learning, or deep learning based algorithms processing the information. This can enable medical imaging data to not only be communicated faster but also be processed quicker. For example, data can be loaded directly to a GPU for faster processing. By utilizing DPUs, CPU resources can be freed up for other processing tasks and improve the overall performance of the system.

FIG. 1 illustrates an example communication system 100 according to at least one example embodiment. The system 100 includes a user device 105, a data processing unit (DPU) 110, a DPU 115, a server 120, a node 125 (e.g., a compute node), a graphics processing unit (GPU) 130, and storage 140. In at least one example embodiment, user device 105 and server 120 correspond to one or more of a Personal Computer (PC), a laptop, a tablet, a smartphone, a server, a collection of servers, or the like. In some embodiments, user device 105 and server 120 may correspond to any appropriate type of device that communicates with other devices connected to a common type of communication network 108. According to embodiments, user device 105 and server 120 may correspond to a GPU, a switch (e.g., a high-speed network switch), a network adapter, a CPU, a memory device, an input/output (I/O) device, other peripheral devices or components on a system-on-chip (SoC), or other devices and components at which a signal is received or measured, etc. As another specific but non-limiting example, user device 105 and server 120 may correspond to servers offering information resources, services, and/or applications to user devices, client devices, or other hosts in the system 100. In at least one embodiment, the communication system 100 is an example system communicating medical imaging data. In such embodiments, medical imaging data can be communicated between the user device 105 and server 120. In at least one embodiment, user device 105 and server 120 are application entities executed on a central processing unit (CPU).

In at least one embodiment, the communication system 100 can communicate information according to a medical imaging and communication protocol. For example, the communication system 100 can communicate information according to a digital imaging and communications in medicine (DICOM) protocol. In some embodiments, the DICOM protocol can be used to store and transmit medical images and enable the integration of medical imaging devices—e.g., scanners, servers, workstations, printers, network hardware, and picture archiving and communications systems (PACS). In such embodiments, the user device 105 and server 120 can be configured to transmit or receive medical imaging data according to a DICOM format. For example, the communication system 100 can communicate medical imaging data including, but not limited to, magnetic resonance imaging (MRI), radiography, computed tomography (CT), radiation therapy, and ultrasonography. In some embodiments, medical imaging data can be communicated from the user device 105 to the server 120. In other embodiments, the server 120 can communicate information to the user device 105—e.g., the communication system 100 can be a bi-directional communication in some embodiments. In at least one embodiment, the user device 105 is an example of a service class user (SCU)—e.g., an application that uses a DICOM network service. In some embodiments, the user device 105 can initiate operations, communications, or set up an association with the server 120. In some embodiments, the user device 105 can be an example of an imaging modality—e.g., image storing SCU, imaging workstation, modality worklist SCU, image query/retrieve SCU. In some embodiments, the server 120 can be an example of a service class provider—e.g., an application that uses the DICOM network service. In some embodiments, the server 120 executes operations requested by another application entity within the DICOM network—e.g., executes operations requested by the SCU. In some embodiments, the server 120 can be an example of a picture archiving and communication system (PACS), image storage SCP, image query/retrieve SCP, or radiology information system. In some embodiments, the server 120 can transmit medical imaging data to node 125 (e.g., a computing node 125).

In at least one embodiment, data processing unit (DPU) 110 can be coupled with the user device 105. FIG. 1B illustrates an example DPU 110. In at least one embodiment, DPU 110 or DPU 115 can be examples of network interface controllers (NICs). In at least one embodiment, DPU 110 or DPU 115 can be examples of a NVIDIA® BlueField® data processing unit (DPU). As illustrated in FIG. 1B, in some embodiments the DPU 110 can include a system-on-chip (SOC) 150, memory devices 175, and memory devices 185. In at least one embodiment, the DPU 110 support directly reading or writing to attached local peripheral memory devices 175 (e.g., NVM express (NVMe) drives or other storage devices) via a storage sub-system in response to remote initiator requests (e.g., content transfer requests received from devices over a network to which the data communication device is connected). In at least one embodiment, the DPU 110 can include memory devices 185 (e.g., a random-access memory (RAM) (e.g., Double Data Rate (DDR) memory)) which are used to transfer content between the data communication device and the memory devices 175, and vice-versa. In some embodiments, the SOC 150 can further include a controller 155 and firmware 165. In some embodiments, the SOC 150 can include a multi-core central processing unit (CPU) in an arm architecture (e.g., ARM 205) to facilitate processing data. In such embodiments, the multi-core CPU arm architecture can couple the controller 155 with the firmware 165. In at least one embodiment, the SOC 150 can include a last level cache (LLC) 180 shared by the controller 155 and firmware 165. In at least one example, the controller 155 is an example of a network interface controller coupling the DPU 110 to the user device 105 or a computer network (e.g., cloud network).

In at least one embodiment, the DPU 110 is configured to receive medical imaging data (e.g., packets) from the user device 105. The DPU 110 can receive the medical imaging data conforming to the DICOM protocol. In some embodiments, the DPU 110 is configured to convert the medical imaging data into a second format that does not conform to the DICOM protocol and transmit the medical imaging data to server 120—e.g., to DPU 115 which can intercept the medical imaging. In some embodiments, the DPU 110 can reduce latencies associated with transmitting the medical imaging data by converting the medical imaging data to the second format. In at least one embodiment, the DPU 110 can encrypt or compress the medical imaging data as described with reference to FIGS. 2 and 3. In at least one embodiment, the DPU 110 can refrain from converting the medical imaging data received to the second format—e.g., the DPU 110 can transmit medical imaging data conforming to the DICOM protocol. In at least one embodiment, the DPU 110 can be configured to transmit medical imaging data conforming to the DICOM protocol. In such embodiments, the DPU 110 can be configured to convert the medical imaging data to the second format based on a data type or instructions provided by a user—e.g., the DPU 110 can have a dedicated pipeline for the DICOM protocol and a separate dedicated pipeline for the second format. For example the DPU 110 can be programmed to transmit all X-ray images received according to the DICOM protocol and transmit all MRI images according to the second format. In at least one embodiment, the DPU 110 can transmit medical imaging data conforming to the DICOM protocol in parallel with medical imaging data that does not conform to the DICOM protocol. In some embodiments, the DPU 110 can transmit the medical imaging data that conforms to the DICOM protocol to a first port of the DPU 115 or server 120 and transmit the medical imaging data that does not conform to the DICOM protocol to a second port of the DPU 115 or server 120.

In at least one embodiment, DPU 115 can be coupled with server 120. In at least one embodiment, the DPU 115 can be configured to intercept messages, packets, or medical imaging data intended for the server 120 from the DPU 110. In such embodiments, the DPU 115 can be configured to ensure any communications to the sever 120 conform to the DICOM protocol. For example, the DPU 115 can intercept a packet transmitted by the DPU 100 that has the second format and reconstruct packets that conform to the DICOM protocol. In at least one embodiment, the DPU 115 can include an embedded application that is associated with or that corresponds to server 120—e.g., that corresponds or is associated with the SCP. In at least one embodiment, the DPU 115 can include a modified version of the server 120 application—e.g., the server application 120 can be executed at the DPU 115 instead of on a server as described with reference to FIG. 5. In at least one embodiment, the DPU 115 can decrypt or decompress the medical imaging data intercepted as described with reference to FIGS. 2 and 3. In some embodiments, the DPU 115 can be configured to perform some preprocessing on the medical imaging data or make the data available to GPU 130 as described with reference to FIGS. 4-7.

In at least one embodiment, node 125 can receive or retrieve medical imaging data from server 120. In some embodiments, the node 125 can manage the workflow that processes the medical imaging data (e.g., medical images). In some embodiments, the node 125 can respond to work requests and process inputs to generate an output—e.g., generate a result. In at least one embodiment, the node 125 is configured to obtain task or request details and record the generated results. In some embodiments, the node 125 can perform a requested computation or inference. In other embodiments, the node 125 can act as a proxy for a requested computation or inference. For example, the node 125 can extract pertinent medical imaging data from the inputs and provide the extract imaging data to a machine learning model (e.g., such as a convolutional neural network (CNN), a deep learning network, a recurrent neural network (RNN), a regression model, a support vector machine, a clustering model, and so on), a deep learning algorithm, or an artificial intelligence (AI) model. In such embodiments, the node 125 can receive (e.g., collect) an output (e.g., results) from the machine learning model, deep learning algorithm, or AI model and format the results as medical documents for storage. In at least one embodiment, the node 125 is an example of an AI model, machine learning model, or deep learning algorithm hosted on a platform. In other embodiments, the node 125 is an example of a standalone system—e.g., a computer-aided detection (CAD) server for mammography screening. In some embodiments, the node 125 is configured to issue instructions such that medical imaging data can be ready for processing or display at or with the help of GPU 130—e.g., the node 125 can issue GPUDirect storage instructions. In some embodiments, this can reduce CPU and memory usage.

In some embodiments, GPU 130 is configured to process or assist with computations or inferences requested by the DPU 115 or by the node 125. In at least one embodiment, storage 140 is configured to store medical imaging information. In some embodiments, storage 140 is an example of a non-volatile memory express (NVMe) drive(s).

FIG. 2 illustrates an example communication system 200 according to at least one example embodiment. The system 200 includes a DPU 110 and a DPU 115 as described with reference to FIG. 1. In at least one embodiment, the DPU 110 and DPU 115 can include an arm 205—e.g., a multi-core central processing unit (CPU) in an arm architecture. In some embodiments, arm 205-a can include a user device application 215 and an encryption component 220. In some embodiments, arm 205-b can include a decryption component 230 and a server device application 235. In some embodiments, DPU 110 can transmit data 250 to DPU 115—e.g., transmit medical imaging data. In some embodiments, the data 250 is associated with a first format (e.g., a DICOM format). In other embodiments, the data 250 is associated with a second format (e.g., a format that does not conform to the DICOM format).

In some embodiments, user device application 215 is an example of an embedded software application. In some embodiments, the user device application 215 is associated with a service class user (SCU)—e.g., the user device application 215 can perform operations that an SCU performs. In such embodiments, the user device application 215 can receive messages, packets, and/or data according to the DICOM format or protocol from user device 105 as described with reference to FIG. 1.

In at least one embodiment, encryption component 220 is configured to encrypt medical imaging data, messages, packets, etc., received from the user device application 215—e.g., encrypt packets received from the user device 105. In some embodiments, the encryption component 220 includes an internet protocol security (e.g., IPSEC or IPSec) module to encrypt the received medical data, messages, or packets. In at least one embodiment, the encryption component 220 is configured to encrypt the messages, packets, or data in hardware. Accordingly, the communication system 200 can refrain from encrypting at an application layer executing at a CPU to reduce latencies. In some embodiments, by encrypting the medical imaging data the encryption component 220 can update the data, messages, or packets to have a second format that does not conform with the DICOM protocol. In at least one embodiment, the DPU 110 can encrypt messages received from any medical imaging modality, including those that do not have built-in transport layer security (TLS), and enable messages to be sent more securely.

In some embodiments, DPU 110 is also configured to filter out or strip excess data or information from incoming data. For example, a DICOM message (e.g., volume, packet, or data set) can include multiple images (e.g., slices), some of which are not used during processing or by a machine learning model or algorithm. In such embodiments, the DPU 110 can filter or strip out the images that are not going to be used and modify the DICOM message to reduce bits transferred to the server 120—e.g. the DPU 110 can be programmed to monitor or look for certain images and strip, remove or ignore the rest. This can reduce latencies and increase transfer times.

In some embodiments, DPU 115 is configured to intercept messages, packets, and/or data intended for server 120. In such embodiments the DPU 115 is configured to ensure messages transmitted to the server 120 conform with the DICOM protocol. In some embodiments, decryption component 230 is configured to decrypt the intercepted messages, packets, or data intended for server 120. In some embodiments, the decryption component 230 includes an internet protocol security (e.g., IPSEC or IPSec) module to decrypt the intercepted medical data, messages, and/or packets.

In some embodiments, server device application 235 is an example of an embedded software application. In some embodiments, the server device application 235 is associated with a service class provider (SCP)—e.g., the server device application 235 can perform operations that the SCP performs. In such embodiments, the server device application 235 can ensure the server 120 receives messages, packets, or data according to the DICOM format or protocol from user device 105 as described with reference to FIG. 1. For example, the decryption component 230 or the server device application 235 can process the messages, packets, or data received corresponding to the second format and reconstruct the messages, packets, or data to correspond to the DICOM format.

Figure 3:
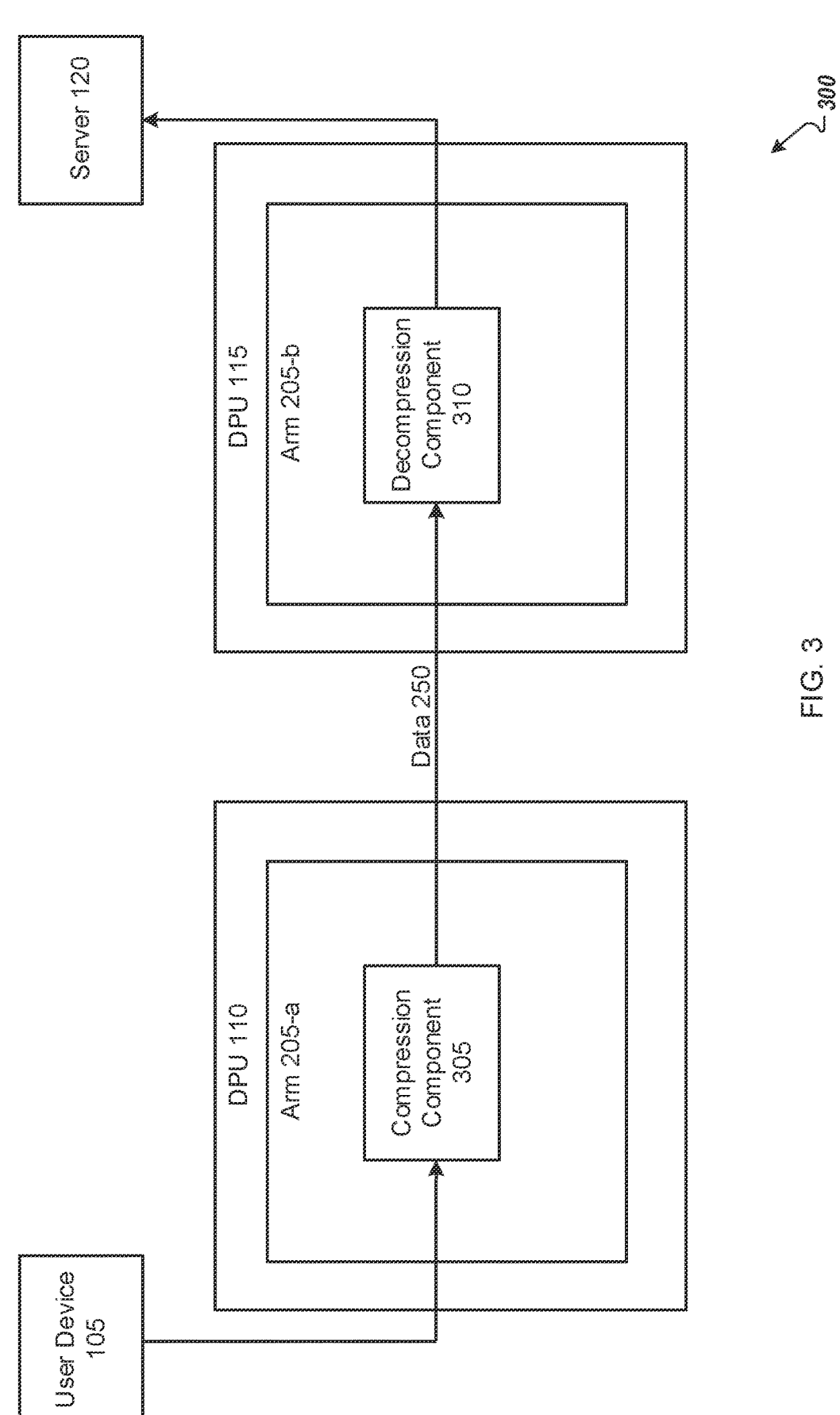
FIG. 3 is an example communication system implementing data processing units (DPUs), in accordance with at least some embodiments.

FIG. 3 illustrates an example communication system 300 according to at least one example embodiment. The system 300 includes a user device 105 coupled to a DPU 110 and a server 120 coupled to a DPU 115 as described with reference to FIG. 1. In at least one embodiment, the DPU 110 and DPU 115 can include an arm 205—e.g., a multi-core central processing unit (CPU) in an arm architecture. In some embodiments, arm 205-a can include a compression component 305. In some embodiments, arm 205-b can include a decompression component 310. In some embodiments, DPU 110 can transmit data 250 to DPU 115—e.g., transmit medical imaging data. In some embodiments, the data 250 is associated with a first format (e.g., a DICOM format). In other embodiments, the data 250 is associated with a second format (e.g., a format that does not conform to the DICOM format). Although not illustrated, DPU 110 can include a user device application 215 and DPU 115 can include a server device application 235 as described with reference to FIG. 2.

In at least one embodiment, compression component 305 is configured to compress medical imaging data received from the user device 105. In such embodiments, the compression component 305 can update the received medical imaging data to correspond to a second format that does not conform with DICOM protocol. In an embodiment, the compression component 305 is configured to decode embedded transfer syntax of received messages, packets, and/or data. For example, the compression component 305 can modify the transfer syntax (e.g., WebP or joint photographic experts group X long-term (JPEG-XL) of the message, medical imaging data, or packet received from the user device 105. In some embodiments, the compression component 305 is configured to encode the modified message, data, and/or packet using a more efficient compression technique to reduce bits transferred to the server 120. In at least one embodiment, the compression component 305 can modify incoming data or messages on a per packet basis without modifying the transfer syntax. In some embodiments, the compression component 305 can use a different compression technique than modifying the transfer syntax e.g., a different compression method or technique that reduces an amount of data transferred while having minimal encoding speed. For example, the compression component 305 can utilize any lossless compression—e.g., run-length encoding (RLE) algorithm, deflate compression algorithm (PNGOUT, OptiPNG, or OxiPNG), Zopfli compression, AV1 image file format, etc.

In at least one embodiment, the compression component 305 can compress incoming messages, packets, or data according to a user defined instruction. For example, the compression component 305 can be programmed to compress any incoming messages, packets, or data according to a lossless JPEX XL algorithm. In such embodiments, if the compression component 305 detects the incoming messages, packets, or data are encoded or compressed with a compression technique other than the user defined compression technique, the compression component 305 can decompress the received message, packet, or data first and then apply the user defined compression technique. In at least one embodiment, the compression component 305 can be programmed according to a rule set such that the compression component 305 can compare a compression technique associated with a message, packet, or data received from the user device 105 with a threshold compression technique. In such embodiments, the compression component 305 can determine whether the compression technique associated with the message, packet, or data transmits less data or has a faster encoding time than the threshold compression technique. For example, the compression component 305 can refrain from decompressing and applying the threshold compression technique if the compression technique associated with the message, packet, or data transmits less data and/or has a faster encoding time than the threshold compression technique. In other examples, the compression component 305 can decompress and apply the threshold comparison technique if the compression technique associated with the message, packet, or data transmits more data and/or has a slower encoding time than the threshold compression technique. In at least one embodiment, the compression component 305 can select a compression technique based on a type of data received from the user device 105. For example, the compression component 305 can select a compression technique based on a format of the data (e.g., whether the data is a JPEG, PNG, or other file format) or based on a imaging modality—e.g., MRI, CT, X-RAY, etc.

In some embodiments, the decompression component 310 is configured to intercept messages, packets, or data 250 having the second format transmitted by the DPU 110 to the server 120—e.g., to reconstruct the original messages, packets, or data that conform with the DICOM protocol. In at least one embodiment, the decompression component 310 is configured to decompress data 250—e.g., reconstruct the original data, message, or packet transmitted by the user device 105. For example, the decompression component 310 can restore custom transfer syntax (e.g., the modified transfer syntax) to the original transfer syntax. In other embodiments, the decompression component 310 can decompress and the recompress the data 250 to restore the original compression of the data, message, or packet transmitted by the user device 105—e.g., the decompression component 310 can decompress and recompress data 250 to go from the threshold compression technique to the original compression technique. After the decompression, the decompression component 310 can transmit the data, packet, or message to the server 120 according to the DICOM protocol.

In embodiments, DPU 110 and DPU 115 may each include components for performing compression/decompression and components for performing encryption/decryption. For example, both encryption and compression may be performed at DPU 110 and both decryption and decompression may be performed at DPU 115.

FIG. 4 illustrates an example communication system 400 according to at least one example embodiment. The system 400 includes a service class user (SCU) 410 and a service class provider (SCP) 415, storage 140, and GPU 130 coupled to a DPU 115 as described with reference to FIG. 1. Although not illustrated, the system 400 can include a DPU (e.g., DPU 110) coupled to the SCU 410 described with reference to FIG. 1. In at least one embodiment, the DPU 115 can include an arm 205—e.g., a multi-core central processing unit (CPU) in an arm architecture. In some embodiments, arm 205-b can include a preprocessing component 405. In some embodiments, SCU 410 (via the DPU 110) can transmit data 250 to DPU 115—e.g., transmit medical imaging data. In some embodiments, the data 250 is associated with a first format (e.g., a DICOM format). In other embodiments, the data 250 is associated with a second format (e.g., a format that does not conform to the DICOM format). Although not illustrated, DPU 110 can include a user device application 215 and DPU 115 can include a server device application 235 as described with reference to FIG. 2. In some embodiments, the SCP 415 is an application entity executing on a CPU—e.g., a service class provider application as described with reference to FIG. 1. Although the SCP 415 is illustrated as executing on a CPU or host (e.g. external to the DPU 115), in at least one embodiment, the SCP 415 can be executed at the DPU 115 as described with reference to FIG. 5. In some embodiments, the DPU 115 is configured to intercept data 250 transmitted by the SCU 410 to the SCU 415.

In at least one embodiment, preprocessing component 405 includes the decompression component 310 as described with reference to FIG. 3—e.g., the preprocessing component can perform transfer syntax conversion and decompress the data 250. In at least one embodiment, the preprocessing component 405 is configured to convert data 250 (e.g., or portions of data 250) into tensors for machine learning (e.g., for input into a trained machine learning model and/or for training of a machine learning model). In at least one embodiment, the preprocessing component 405 can convert data 250 (e.g., or portions of data 250) into a NumPy data structure for machine learning. In some embodiments, the preprocessing component is configured to modify DICOM elements, add elements, change values, or even delete data. In some embodiments, the preprocessing component 405 can modify data before it is utilized in downstream tasks (e.g., at the node 125 or a machine learning model as described with reference to FIG. 1)

In at least one embodiment, data 250 can include metadata (e.g., headers) and pixel data (e.g., raw pixel data). In some embodiments, the preprocessing component 405 is configured to store the raw pixel data and/or the tensors in storage 140. In such embodiments, the preprocessing component 405 can make the pixel data and tensors available for a workflow manager as described with reference to FIGS. 6 and 7. In some embodiments, the preprocessing component 405 can transmit the pixel data or tensors to the GPU 130, bypassing transmitting the data to SCP 415 and/or the storage 140. In at least one embodiment, the preprocessing component 405 is configured to extract the metadata (e.g., the header or DICOM header) to JavaScript Object Notation (JSON) files—e.g., to conform to the DICOM JSON model.

In some embodiments, the preprocessing component 405 can extract the header to store at storage 140. In other embodiments, the preprocessing component 405 can extract the header and transmit the header to the SCP 415—e.g., to the SCP 415 executing at the CPU or on an SCP executing on DPU 115. In at least one embodiment, the preprocessing component 405 can filter out portions of data 250 (e.g., portions of the pixel data) based on the metadata header and user specified criterion—e.g., user instructions indicating a type of pixel data or specific pixel data to process. For example, the preprocessing component 405 can receive data 250 and extract pixel data from the data 250 received. In at least one embodiment, the user criterion could be determined based on the metadata header. For example, the user criterion could be based on a type of modality (e.g., CT, Mill, ultrasound (US), etc.), a description of a study (e.g., StudyDescritpion 0008), a description of a series (e.g., SeriesDescription 0008), or an image type (e.g., 0008). In some embodiments, the preprocessing component 250 can transmit the remaining data 250 (e.g., the DICOM header) to SCP 415. In such embodiments, the SCP 415 can determine whether to utilize the pixel data based on the user criterion. In some embodiments, an SCP executing on DPU 115 can determine whether to utilize the pixel data based on the user criterion. In some embodiments, if the SCP 415 or DPU 115 determine the user criterion is satisfied, the DPU 115 can store the pixel data at storage 140 or transmit the pixel data to the GPU 130. In some embodiments, the DPU 115 can transmit the pixel data to the SCP 415 if the user criterion is satisfied. In other embodiments, if the DPU 115 or the SCP 415 determine the user criterion is not satisfied, the DPU 115 can refrain from storing the data 250 at the storage 140— e.g., the DPU 115 can drop the data 250. By transmitting the header rather than all of data 250, the DPU 115 can reduce transfer times and improve a latency of system 400.

Figure 5:
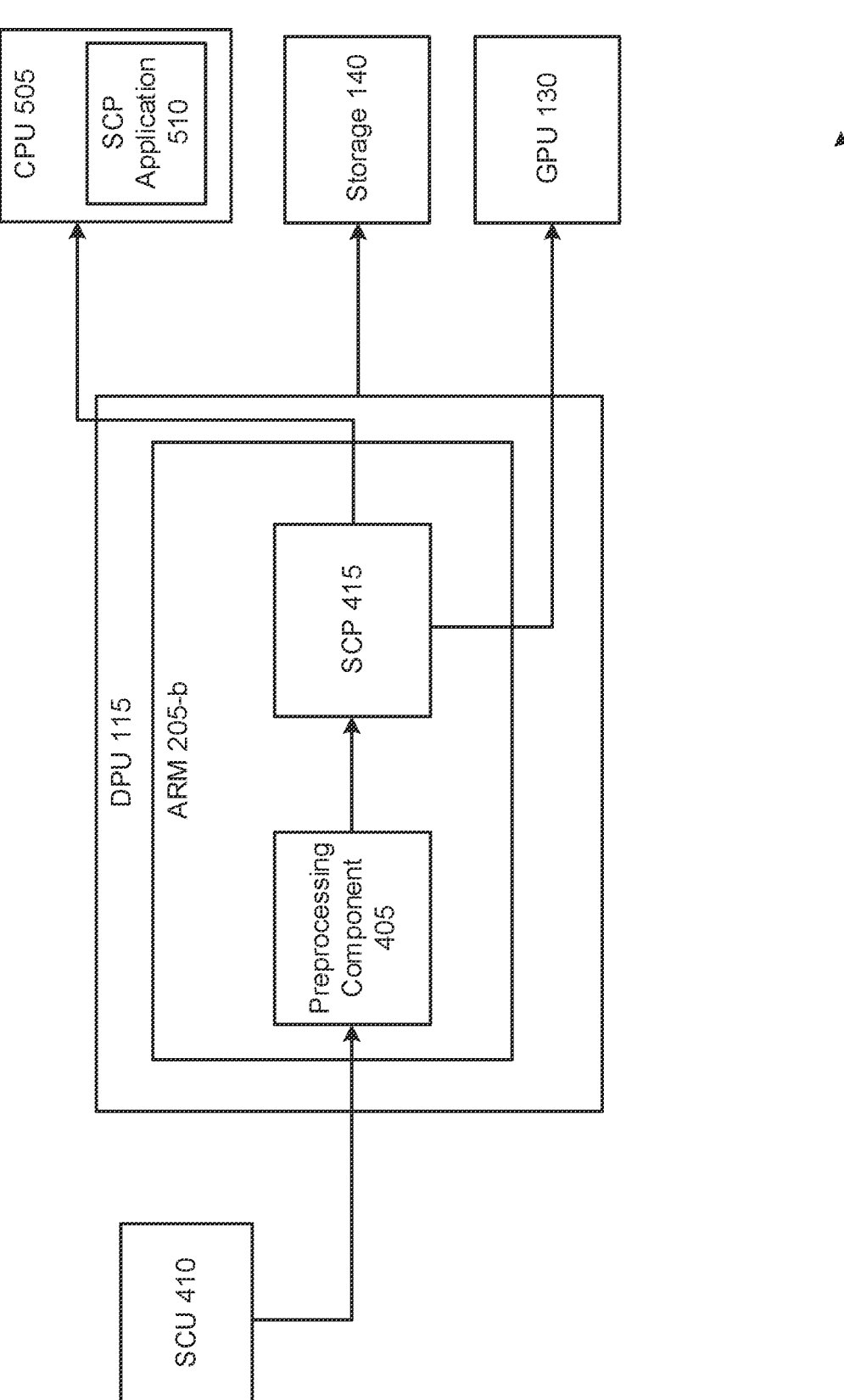
FIG. 5 is an example communication system implementing data processing units (DPUs), in accordance with at least some embodiments.

FIG. 5 illustrates an example communication system 500 according to at least one example embodiment. The system 500 includes a service class user (SCU) 410 and a CPU 505 storage 140, and GPU 130 coupled to a DPU 115 as described with reference to FIG. 1. The DPU 115 can include class provider (SCP) 415 and the CPU 505 can include SCP application 510. Although not illustrated, the system 500 can include a DPU (e.g., DPU 110) coupled to the SCU 410 as described with reference to FIG. 1. In at least one embodiment, the DPU 115 can include an arm 205— e.g., a multi-core central processing unit (CPU) in an arm architecture. In some embodiments, arm 205-*b* can include a preprocessing component 405. In some embodiments, SCU 410 (via the DPU 110) can transmit data 250 to DPU 115—e.g., transmit medical imaging data. In some embodiments, the data 250 is associated with a first format (e.g., a DICOM format). In other embodiments, the data 250 is associated with a second format (e.g., a format that does not conform to the DICOM format). In some embodiments, the DPU 115 is configured to intercept data 250 transmitted by the SCU 410 to the SCU 415.

In at least one embodiment, the DPU 115 is configured to execute the SCP 415—e.g., SCP 415 can be executed at the DPU 115 instead of at the CPU 505. In such embodiments, SCP 415 at the DPU 115 can perform DICOM negotiations, associations, or any other operations associated with the DICOM protocol. In at least one embodiment, the SCP 415 is modified to execute on the DPU 115. For example, the SCP 415 executing at the DPU 115 can enable the DPU 115 to store DICOM messages, data, or packets directly at storage by zeroing out binary data fields (OB, OW) without violating the DICOM protocol. By preprocessing and transmitting the data 250 to the storage 140 directly, the DPU 115 can reduce transfer times by refraining from copying data 250 from DPU 115 to CPU 505 and then to storage 140. In some embodiments, the system 500 can reduce a processing time of data 250 by executing the SCP 415 at the DPU 115—e.g., the SCP 415 can immediately start processing data at the DPU 115 instead of waiting for a copy of data 250 to be transmitted from the DPU 115 to the CPU 505. In some embodiments, the SCP can be executed at both the DPU 115 and at the CPU 505. For example, SCP 415 can perform typical DICOM protocol operations while an SCP application 510 executing at the CPU 505 can perform additional tasks—e.g., the SCP application 510 can perform subsequent read operations, monitor storage of incoming data 250, packets, or messages, or enable direct storage such that the CPU 505 can make data 250 available to the GPU 130 for processing.

In some embodiments, the preprocessing component 405 can also include a study filter application that modifies, changes values of, or deletes DICOM elements according to a user defined instruction. In some embodiments, the study filter application of the preprocessing component 405 can zero out pixel data of unwanted instances—e.g., the study filter application can drop pixel data that will be unused as described with reference to FIG. 4. To filter data 250, the preprocessing component 405 can extract metadata (e.g., the headers) and provide the headers to the study filter application. In at least one embodiment, the preprocessing component 405 includes a data plane development kit (DPDK) to process data 250 according to the user defined instruction In at least one embodiment, the preprocessing component 405 can include a regular expression (RegEx) engine. In such embodiments, the RegEx engine can execute user defined rules to determine whether to transmit data 250 (e.g., or portions of data 250) to the SCP 415. In some embodiments, the RegEx engine can transmit all of data 250 to the SCP 415 if the data 250 satisfies the user defined rules. In other embodiments, the RegEx engine can transmit a portion of data 250 (e.g., the metadata or headers) to the SCP 415 if the data 250 does not satisfy the user defined rules. In some embodiments, the RegEx engine can refrain from transmitting any portion of data 250 to the SCP 415—e.g., the RegEx engine can drop the data 250. In such embodiments, the data 250 (e.g., unwanted DICOM studies) can have their binary data fields (OB, OW) zeroed-out.

Figure 6:
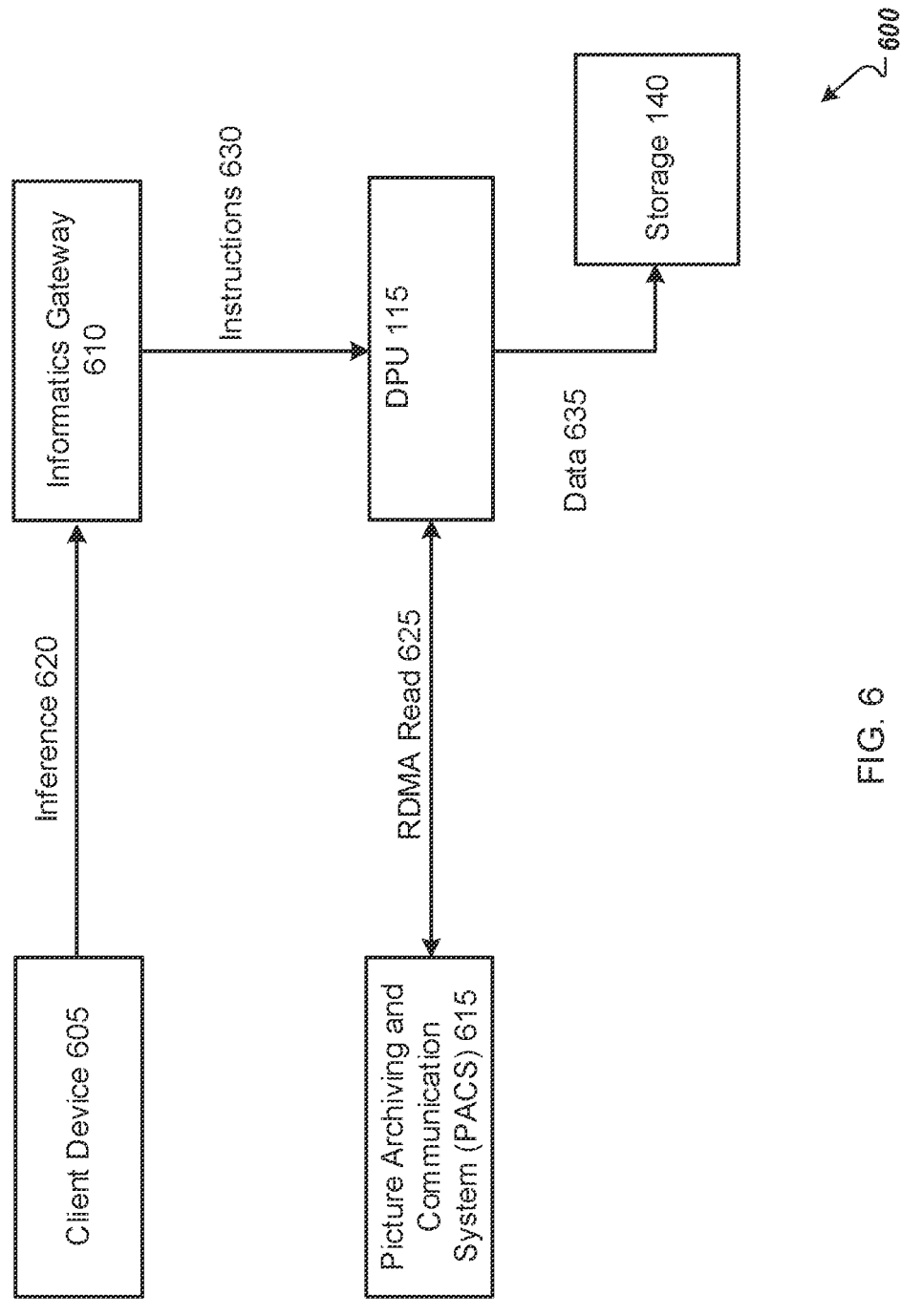
FIG. 6 is an example communication system implementing data processing units (DPUs), in accordance with at least some embodiments.

FIG. 6 illustrates an example communication system 600 according to at least one example embodiment. The system 600 includes a client device 605, an informatics gateway 610, a picture archiving and communication system (PACS) 615, a data processing unit (DPU) 115, and storage 140. In some embodiments, system 600 illustrates retrieval of a DICOM instance or packet using remote direct memory access (RDMA).

In some embodiments, client device 605 can initiate a request or operation. For example, the client device 605 can request data, request an inference, or any other command associated with a DICOM protocol. In some embodiments, the client device 605 can be an example of a user device 105 or SCU 410 as described with reference to FIGS. 1 and 4. In some embodiments, the client device 605 can request an inference 620 from informatics gateway 610.

In at least one embodiment, the informatics gateway 610 is an example of a DICOM server. In some embodiments, the informatics gateway 610 can monitor for incoming DICOM requests or studies. In some embodiments, the informatics gateway 610 can be an example of a SCU 410 as described with reference to FIG. 4. In other embodiments, the informatics gateway 610 can be an example of a SCP 415 as described with reference to FIG. 4. In some embodiments, the informatics gate 610 can transmit an instruction(s) 630 to the DPU 115 responsive to receiving the inference 620 request. In some embodiments, the informatics gateway 610 transmits instruction(s) 630 to instruct DPU 115 to initiate an RDMA read 625 and/or retrieve a service-object (SOP) instance.

In at least one embodiment, DPU 115 is configured to receive instructions 630 from the informatics gateway 610. In some embodiments, the DPU 115 is configured to initiate an RDMA read 625 in response to receiving instructions 630. In at least one embodiment the DPU 115 can read data from a picture archiving and communication system (PACS) 615. In at least one embodiment, the PACS 615 is medical imaging technology that can store and provide access to medical imaging from multiple modalities. In at least one embodiment, the PACS 615 is configured to store and transfer medical imaging according to the DICOM protocol.

In some embodiments, the DPU 115 can retrieve data 635 (e.g., data or medical imaging associated with the inference 620) responsive to initiating the RDMA read 625. In at least one embodiment, the DPU 115 is configured to store data 635 at storage 140 responsive to receiving data 635 from the PACS 615. In such embodiments, the DPU 115 can accelerate the storage of data 635 as the data 635 is stored without being sent to the informatics gateway 610 for additional processing—e.g., utilizing the DPU 115 can reduce resources and memory usage of the informatics gateway (e.g., of a CPU).

Figure 7:
FIG. 7 is an example communication system implementing data processing units (DPUs), in accordance with at least some embodiments.

FIG. 7 illustrates an example communication system 700 according to at least one example embodiment. The system 700 includes an informatics gateway 610, a picture archiving and communication system (PACS) 615, a data processing unit (DPU) 110, DPU 115, GPU 130, workflow manager 705, and shared storage 710. In some embodiments, system 700 illustrates an example request being executed and processed by the DPUs 110 and 115.

In at least one embodiment, PACS 615 is configured to transmit a message 715 to the informatics gateway 610 and/or the DPU 110. In at least one embodiment, message 715 is an example of a DICOM message service element (DEVISE). In some embodiments, the message 715 includes a DICOM study—e.g., a collection of images, presentation states, or SR documents logically related for purpose of diagnosing a patient generated at one or more modalities. For example, the PACS 615 can transmit a DICOM study that includes a collection of X-Ray images related to a patient's broken leg.

In at least one embodiment, DPU 110 is configured to store DICOM files at the shared storage 710. For example, the DPU 110 can store the message 715 and the DICOM study included in the message 715 received from the PACS 615. In at least one embodiment, the DPU 110 can notify the informatics gateway 610 the message 715 is stored at the shared storage 710. In such embodiments, the informatics gateway 610 can transmit a notification 725 to the workflow manager 705. In some embodiments, the notification 725 can indicate the message 715 is stored at the shared storage 710 and is ready for processing.

In some embodiments, workflow manager 705 is configured to execute requests or tasks based on incoming studies or messages 715. In some embodiments, the workflow manager 705 includes one or more logic devices to process incoming data and execute assigned or user defined algorithms on the data. For example, the workflow manager 705 can receive the notification 725 and begin executing the workflow indicated in the notification or message 715. In some embodiments, the workflow manager 705 can transmit instructions to the DPU 115 to retrieve data 720 and make it available for the GPU 130. In such embodiments, the DPU 115 is configured to initiate a RDMA read 730 responsive to receiving instructions from the workflow manager 705. In some embodiments, when the DPU 115 receives the data 720, the DPU 115 can transmit the data 720 to the GPU 130. Accordingly, the workflow manager 705 can process the data 720 and execute assigned or user defined algorithms on the data 720 at the GPU 130. By utilizing the DPUs 110 and 115, the system 700 can accelerate the storage and retrieval of data 720.

FIG. 8 illustrates an example flow diagram of a method 800 for accelerating transfer and processing of medical imaging data using data processing units (DPUs), according to at least one embodiment. The method 800 can be performed by processing logic comprising hardware, software, firmware, or any combination thereof. In at least one embodiment, the method 800 is performed by the DPU 110 or DPU 115 as described with reference to FIG. 1. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other diagrams illustrating a method for accelerating transfer and processing medical imaging data using DPUs are possible.

At operation 805, a data processing unit (e.g., DPU) or processing logic can receive one or more packets for medical imaging data, the one or more packets having a first format that conforms to a medical imaging data protocol. In at least one embodiment, the first format or protocol is a digital imaging and communication in medicine (DICOM) protocol. In some embodiments, the DPU can be coupled to a central processing unit (CPU) or a service class user (SCU). In such embodiments, the CPU or SCU can transmit or generate the one or more packets and request an operation associated with processing the medical imaging data.

At operation 810, the DPU or processing logic can process the one or more packets into one or more updated packets having a second format that does not conform to the medical imaging data protocol. In at least one embodiment, the DPU can select an encryption technique from one or more encryption techniques based at least in part on a criterion. In some embodiments, the criterion is a user defined criterion—e.g., the user can program the DPU to select an encryption technique, program the DPU to select an encryption technique based on a data type of the packets, or program the DPU to select an encryption technique. In some embodiments, the DPU can process the one or more packets by encrypting the one or more packets—e.g., the DPU can update the one or more packets into the second format and apply an encryption technique before transmitting the one or more updated packets. The encryption can be performed using a selected encryption technique.

In at least one embodiment, the DPU can select a compression technique from one or more compression techniques based at least in part on a criterion. In some embodiments, the criterion is a user defined criterion—e.g., the user can program the DPU to select a compression technique, program the DPU to select a compression technique based on a data type of the packets, or program the DPU to select the most efficient compression technique. In at least one embodiment, the DPU can compress the one or more packets with the selected compression technique. In at least one embodiment, the DPU can identify a second compression technique associated with the one or more packets (e.g., that has already been applied to the one or more packets). In such embodiments, the DPU can compare the second compression technique with the one or more compression techniques and select the compression technique in response to the comparison—e.g., select the best compression technique that reduces latencies. In some embodiments, the DPU can identify a type of data associated with the one or more packets, where the DPU is to select the compression technique in response to identifying the type of data.

At operation 815, the DPU or processing logic, can transmit the one or more updated packets to a target device configured to receive packets having the first format. In some embodiments, the target device can be a service class provider (SCP) or a CPU. In some embodiments, the target device is coupled to a second DPU (e.g., DPU 115) configured to intercept communications intended for the target device. In at least one embodiment, the DPU can receive a second set of packets for medical image data, the second set of packets having the first format that conforms to the medical data protocol. In such embodiments, the DPU can process the second set of packets into a second set of updated packets having the first format that conforms to the medical data protocol and transmit the second set of updated packets to a first port of the target device, where the DPU is to transmit the one or more updated packets to a second port of the target device. That is, the DPU can either communicate the one or more packets according to the DICOM protocol or communicate the one or more packets in a second format that is different than the DICOM protocol.

Figure 9:
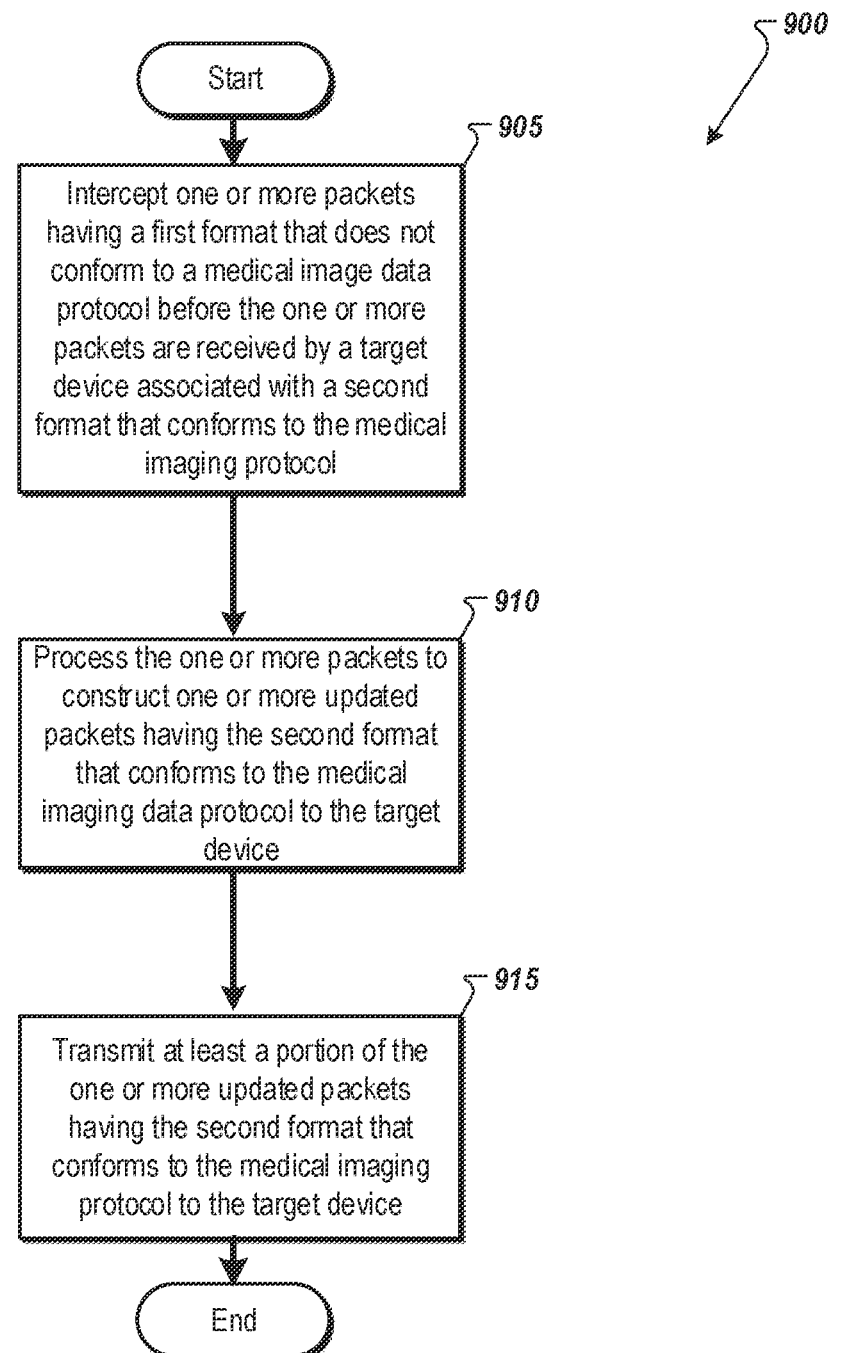
FIG. 9 is a flow diagram of a method for accelerating transfer and processing of imaging information using data processing units, in accordance with at least some embodiments.

FIG. 9 illustrates an example flow diagram of a method 900 for accelerating transfer and processing of medical imaging data using data processing units (DPUs), according to at least one embodiment. The method 900 can be performed by processing logic comprising hardware, software, firmware, or any combination thereof. In at least one embodiment, the method 900 is performed by the DPU 110 or DPU 115 as described with reference to FIG. 1. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other diagrams illustrating a method for accelerating transfer and processing medical imaging data using DPUs are possible.

At operation 905, a data processing unit (e.g., DPU) or processing logic, can intercept one or more packets having a first format that does not conform to a medical image data protocol before the one or more packets are received by a target device associated with a second format that conforms to the medical image data protocol. In at least one embodiment, the protocol is a digital imaging and communications in medicine (DICOM) protocol. In at least one embodiment, the DPU can intercept the one or more packets from a second DPU.

At operation 910 the DPU or processing logic, can process the one or more packets to construct one or more updated packets having the second format that conforms to the medical imaging data protocol. In some embodiments, the DPU is to construct the one or more updated packets by decrypting the one or more packets. In at least one embodiment, the DPU can identify a first portion of the one or more updated packets associated with metadata. In such embodiments, the DPU can identify a second portion of the one or more updated packets associated with data—e.g., identify pixel data. In some embodiments, the DPU can transmit a first portion to the target device responsive to identifying the first portion. In some embodiments, the DPU can transmit the second portion directly to a first device, where the first device is a graphics processing unit (GPU). In some embodiments, the second portion is not transmitted to the target device. In some embodiments, the DPU is configured to compare the second portion with a threshold criterion—e.g., compare the second portion with a user defined criterion that indicates which data to process and perform operations on. In such embodiments, the DPU can determine the second portion satisfies the threshold criterion and transmit the second portion to the target device responsive to determining the second portion satisfies the threshold criterion. In at least one embodiment, the DPU can determine the second portion fails to satisfy the threshold criterion and refrain from transmitting the second portion to the target device—e.g., the pixel data does not correspond to data a user wants to process. In some embodiments, the DPU can store the one or more updated packets in a storage responsive to determining the second portion satisfies the threshold criterion. In some embodiments, the DPU can refrain from storing the one or more updated packets in the storage responsive to determining the second portion fails to satisfy the threshold criterion. In least one embodiment, the DPU is to convert the second portion to a tensor before transmitting the second portion to a third device. In some embodiments, the DPU is to process the one or more packets at a component executing an application associated with the target device—e.g., at an embedded application associated with the SCP. In some embodiments, the DPU is configured to process the one or more packets at a first component executing an application where the target device comprises a second component executing the application—e.g., the DPU includes a modified instance of the SCP and a CPU coupled with the DPU is executing an embedded application associated with the modified SCP. In at least one embodiment, the DPU is to filter the one or more packets at a second application, where the filtering is associated with pixel data of the one or more packets, and where the DPU is to process the one or more updated packets at the first component in response to filtering the one or more packets.

At operation 915, the DPU or processing logic, can transmit at least a portion of the one or more updated packets having the second format that conforms to the medical imaging data protocol to the target device. In some embodiments, the DPU is to receive, from a server coupled with the DPU, a request to initiate a remote direct memory access (RDMA) read. In such embodiments, the DPU is to read, from a picture archiving and communication system (PACS), data corresponding to the RDMA read in response to receiving the request. In some embodiments, the DPU is to store the data at a storage device coupled with the second DPU in response to reading the data.

Figure 10:
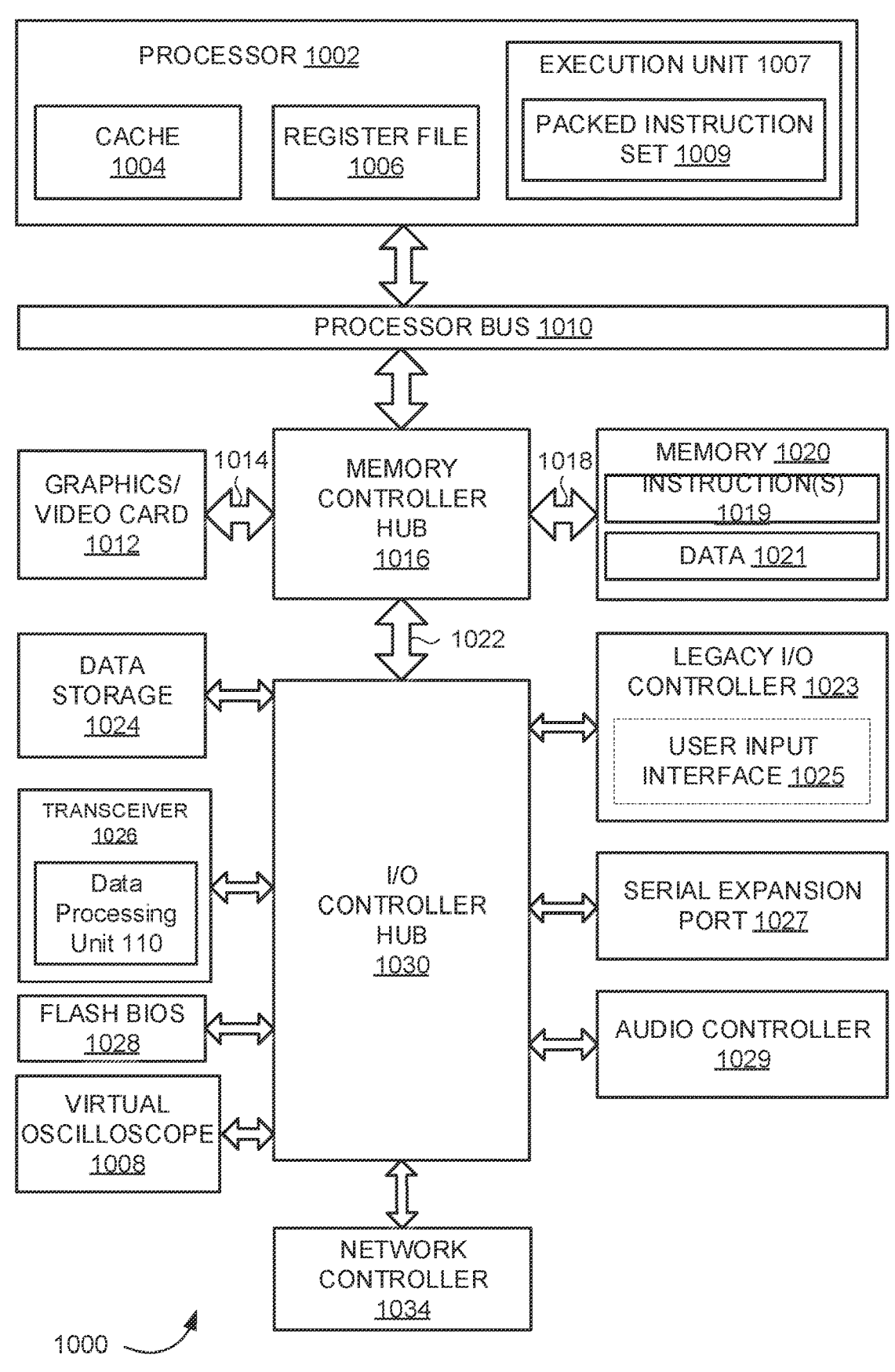
FIG. 10 illustrates an example computer system for accelerating transfer and processing of imaging information using data processing units, in accordance with at least some embodiments.

FIG. 10 illustrates a computer system 1000 in accordance with at least one embodiment. In at least one embodiment, computer system 1000 may be a system with interconnected devices and components, an SOC, or some combination. In at least one embodiment, computer system 1000 is formed with a processor 1002 that may include execution units to execute an instruction. In at least one embodiment, computer system 1000 may include, without limitation, a component, such as processor 1002, to employ execution units including logic to perform algorithms for processing data. In at least one embodiment, computer system 1000 may include processors, such as PENTIUM® Processor family, Xeon™, Itanium®, XScale™ and/or StrongARM™, Intel® Core™, or Intel® Nervana™ microprocessors available from Intel Corporation of Santa Clara, California, although other systems (including PCs having other microprocessors, engineering workstations, set-top boxes and like) may also be used. In at least one embodiment, computer system 1000 may execute a version of WINDOWS' operating system available from Microsoft Corporation of Redmond, Wash., although other operating systems (UNIX and Linux for example), embedded software, and/or graphical user interfaces, may also be used.

In at least one embodiment, computer system 1000 may be used in other devices such as handheld devices and embedded applications. Some examples of handheld devices include cellular phones, Internet Protocol devices, digital cameras, personal digital assistants ("PDAs"), and handheld PCs. In at least one embodiment, embedded applications may include a microcontroller, a digital signal processor (DSP), an SoC, network computers ("NetPCs"), set-top boxes, network hubs, wide area network ("WAN") switches, or any other system that may perform one or more instructions. In an embodiment, computer system 1000 may be used in devices such as graphics processing units (GPUs), network adapters, central processing units and network devices such as switch (e.g., a high-speed direct GPU-to-GPU interconnect such as the NVIDIA GH100 NVLINK or the NVIDIA Quantum 2 64 Ports InfiniBand NDR Switch).

In at least one embodiment, computer system 1000 may include, without limitation, processor 1002 that may include, without limitation, one or more execution units 1007 that may be configured to execute a Compute Unified Device Architecture ("CUDA") (CUDA® is developed by NVIDIA Corporation of Santa Clara, CA) program. In at least one embodiment, a CUDA program is at least a portion of a software application written in a CUDA programming language. In at least one embodiment, computer system 1000 is a single processor desktop or server system. In at least one embodiment, computer system 1000 may be a multiprocessor system. In at least one embodiment, processor 1002 may include, without limitation, a CISC microprocessor, a RISC microprocessor, a VLIW microprocessor, a processor implementing a combination of instruction sets, or any other processor device, such as a digital signal processor, for example. In at least one embodiment, processor 1002 may be coupled to a processor bus 1010 that may transmit data signals between processor 1002 and other components in computer system 1000.

In at least one embodiment, processor 1002 may include, without limitation, a Level 1 ("L1") internal cache memory ("cache") 1004. In at least one embodiment, processor 1002 may have a single internal cache or multiple levels of internal cache. In at least one embodiment, cache memory may reside external to processor 1002. In at least one embodiment, processor 1002 may also include a combination of both internal and external caches. In at least one embodiment, a register file 1006 may store different types of data in various registers including, without limitation, integer registers, floating point registers, status registers, and instruction pointer register.

In at least one embodiment, execution unit 1007, including, without limitation, logic to perform integer and floating point operations, also resides in processor 1002. Processor 1002 may also include a microcode ("ucode") read only memory ("ROM") that stores microcode for certain macro instructions. In at least one embodiment, an execution unit of processor 1002 may include logic to handle a packed instruction set 1009. In at least one embodiment, by including packed instruction set 1009 in an instruction set of a general-purpose processor 1002, along with associated circuitry to execute instructions, operations used by many multimedia applications may be performed using packed data in a general-purpose processor 1002. In at least one embodiment, many multimedia applications may be accelerated and executed more efficiently by using full width of a processor's data bus for performing operations on packed data, which may eliminate a need to transfer smaller units of data across a processor's data bus to perform one or more operations one data element at a time.

In at least one embodiment, an execution unit may also be used in microcontrollers, embedded processors, graphics devices, DSPs, and other types of logic circuits. In at least one embodiment, computer system 1000 may include, without limitation, a memory 1020. In at least one embodiment, memory 1020 may be implemented as a DRAM device, an SRAM device, flash memory device, or other memory device. Memory 1020 may store instruction(s) 1019 and/or data 1021 represented by data signals that may be executed by processor 1002.

In at least one embodiment, a system logic chip may be coupled to processor bus 1010 and memory 1020. In at least one embodiment, the system logic chip may include, without limitation, a memory controller hub ("MCH") 1016, and processor 1002 may communicate with MCH 1016 via processor bus 1010. In at least one embodiment, MCH 1016 may provide a high bandwidth memory path 1018 to memory 1020 for instruction and data storage and for storage of graphics commands, data and textures. In at least one embodiment, MCH 1016 may direct data signals between processor 1002, memory 1020, and other components in computer system 1000 and to bridge data signals between processor bus 1010, memory 1020, and a system I/O 1022. In at least one embodiment, system logic chip may provide a graphics port for coupling to a graphics controller. In at least one embodiment, MCH 1016 may be coupled to memory 1020 through high bandwidth memory path 1018, and graphics/video card 1012 may be coupled to MCH 1016 through an Accelerated Graphics Port ("AGP") interconnect 1014.

In at least one embodiment, computer system 1000 may use system I/O 1022 that is a proprietary hub interface bus to couple MCH 1016 to I/O controller hub ("ICH") 1030. In at least one embodiment, ICH 1030 may provide direct connections to some I/O devices via a local I/O bus. In at least one embodiment, a local I/O bus may include, without limitation, a high-speed I/O bus for connecting peripherals to memory 1020, a chipset, and processor 1002. Examples may include, without limitation, an audio controller 1029, a firmware hub ("flash BIOS") 1028, a transceiver 1026, a data storage 1024, a legacy I/O controller 1023 containing a user input interface 1025 and a keyboard interface, a serial expansion port 1027, such as a USB, and a network controller 1034. Data storage 1024 may comprise a hard disk drive, a floppy disk drive, a CD-ROM device, a flash memory device, or other mass storage device.

In at least one embodiment, FIG. 10 illustrates a system, which includes interconnected hardware devices or "chips" in a transceiver 1026—e.g., the transceiver 1026 includes a chip-to-chip interconnect. In some embodiments, transceiver 1026 includes or is part of a system 100 as described with reference to FIG. 1. In at least one embodiment, FIG. 10 may illustrate an exemplary SoC. In at least one embodiment, devices illustrated in FIG. 10 may be interconnected with proprietary interconnects, standardized interconnects (e.g., PCIe), or some combination thereof and utilize a GRS link. In at least one embodiment, one or more components of system 1000 are interconnected using compute express link ("CXL") interconnects. In an embodiment, the transceiver 1026 can include a DPU 110 or DPU 115 as described with reference to FIG. 1. In such embodiments, the DPU 110 or DPU 115 can accelerate transfer and processing of medical imaging data communicated as described with reference to FIGS. 2-7.

Other variations are within spirit of present disclosure. Thus, while disclosed techniques are susceptible to various modifications and alternative constructions, certain illustrated embodiments thereof are shown in drawings and have been described above in detail. It should be understood, however, that there is no intention to limit the disclosure to a specific form or forms disclosed, but on the contrary, the intention is to cover all modifications, alternative constructions, and equivalents falling within the spirit and scope of the disclosure, as defined in appended claims.

Use of terms "a" and "an" and "the" and similar referents in the context of describing disclosed embodiments (especially in the context of following claims) are to be construed to cover both singular and plural, unless otherwise indicated herein or clearly contradicted by context, and not as a definition of a term. Terms "comprising," "having," "including," and "containing" are to be construed as open-ended terms (meaning "including, but not limited to,") unless otherwise noted. "Connected," when unmodified and referring to physical connections, is to be construed as partly or wholly contained within, attached to, or joined together, even if there is something intervening. Recitations of ranges of values herein are merely intended to serve as a shorthand method of referring individually to each separate value falling within the range, unless otherwise indicated herein, and each separate value is incorporated into the specification as if it were individually recited herein. In at least one embodiment, the use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but subset and corresponding set may be equal.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in an illustrative example of a set having three members, conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, the term "plurality" indicates a state of being plural (e.g., "a plurality of items" indicates multiple items). In at least one embodiment, the number of items in a plurality is at least two, but can be more when so indicated either explicitly or by context. Further, unless stated otherwise or otherwise clear from context, the phrase "based on" means "based at least in part on" and not "based solely on."

Operations of processes described herein can be performed in any suitable order unless otherwise indicated herein or otherwise clearly contradicted by context. In at least one embodiment, a process such as those processes described herein (or variations and/or combinations thereof) is performed under control of one or more computer systems configured with executable instructions and is implemented as code (e.g., executable instructions, one or more computer programs or one or more applications) executing collectively on one or more processors, by hardware or combinations thereof. In at least one embodiment, code is stored on a computer-readable storage medium, for example, in the form of a computer program comprising a plurality of instructions executable by one or more processors. In at least one embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In at least one embodiment, code (e.g., executable code or source code) is stored on a set of one or more non-transitory computer-readable storage media having stored thereon executable instructions (or other memory to store executable instructions) that, when executed (i.e., as a result of being executed) by one or more processors of a computer system, cause a computer system to perform operations described herein. In at least one embodiment, a set of non-transitory computer-readable storage media comprises multiple non-transitory computer-readable storage media and one or more of individual non-transitory storage media of multiple non-transitory computer-readable storage media lack all of the code while multiple non-transitory computer-readable storage media collectively store all of the code. In at least one embodiment, executable instructions are executed such that different instructions are executed by different processors.

Accordingly, in at least one embodiment, computer systems are configured to implement one or more services that singly or collectively perform operations of processes described herein and such computer systems are configured with applicable hardware and/or software that enable the performance of operations. Further, a computer system that implements at least one embodiment of present disclosure is a single device and, in another embodiment, is a distributed computer system comprising multiple devices that operate differently such that distributed computer system performs operations described herein and such that a single device does not perform all operations.

Use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

All references, including publications, patent applications, and patents, cited herein are hereby incorporated by reference to the same extent as if each reference were individually and specifically indicated to be incorporated by reference and were set forth in its entirety herein.

In description and claims, terms "coupled" and "connected," along with their derivatives, may be used. It should be understood that these terms may not be intended as synonyms for each other. Rather, in particular examples, "connected" or "coupled" may be used to indicate that two or more elements are in direct or indirect physical or electrical contact with each other. "Coupled" may also mean that two or more elements are not in direct contact with each other, but yet still co-operate or interact with each other.

Unless specifically stated otherwise, it may be appreciated that throughout specification terms such as "processing," "computing," "calculating," "determining," or like, refer to action and/or processes of a computer or computing system, or similar electronic computing device, that manipulate and/or transform data represented as physical, such as electronic, quantities within computing system's registers and/or memories into other data similarly represented as physical quantities within computing system's memories, registers or other such information storage, transmission or display devices.

In a similar manner, the term "processor" may refer to any device or portion of a device that processes electronic data from registers and/or memory and transform that electronic data into other electronic data that may be stored in registers and/or memory. A "computing platform" may comprise one or more processors. As used herein, "software" processes may include, for example, software and/or hardware entities that perform work over time, such as tasks, threads, and intelligent agents. Also, each process may refer to multiple processes, for carrying out instructions in sequence or in parallel, continuously or intermittently. In at least one embodiment, terms "system" and "method" are used herein interchangeably insofar as the system may embody one or more methods and methods may be considered a system.

In the present document, references may be made to obtaining, acquiring, receiving, or inputting analog or digital data into a subsystem, computer system, or computer-implemented machine. In at least one embodiment, the process of obtaining, acquiring, receiving, or inputting analog and digital data can be accomplished in a variety of ways such as by receiving data as a parameter of a function call or a call to an application programming interface. In at least one embodiment, processes of obtaining, acquiring, receiving, or inputting analog or digital data can be accomplished by transferring data via a serial or parallel interface. In at least one embodiment, processes of obtaining, acquiring, receiving, or inputting analog or digital data can be accomplished by transferring data via a computer network from providing entity to acquiring entity. In at least one embodiment, references may also be made to providing, outputting, transmitting, sending, or presenting analog or digital data. In various examples, processes of providing, outputting, transmitting, sending, or presenting analog or digital data can be accomplished by transferring data as an input or output parameter of a function call, a parameter of an application programming interface or inter-process communication mechanism.

Although descriptions herein set forth example embodiments of described techniques, other architectures may be used to implement described functionality, and are intended to be within the scope of this disclosure. Furthermore, although specific distributions of responsibilities may be defined above for purposes of description, various functions and responsibilities might be distributed and divided in different ways, depending on circumstances.

Furthermore, although the subject matter has been described in language specific to structural features and/or methodological acts, it is to be understood that subject matter claimed in appended claims is not necessarily limited to specific features or acts described. Rather, specific features and acts are disclosed as exemplary forms of implementing the claims.

What is claimed is:

1. A system comprising:
a first data processing unit (DPU) comprising dedicated hardware logic, the DPU configured to:
receive one or more packets for medical imaging data, the one or more packets having a first format that conforms to a medical imaging data protocol;
transform, via the dedicated hardware logic of the DPU performing hardware-level packet transformation operations, bypassing a kernel layer of the system, the one or more packets into one or more updated packets having a second format that does not conform to the medical imaging data protocol, wherein bypassing the kernel layer reduces latency compared to processing through the kernel layer; and
transmit the one or more updated packets to a second DPU coupled to a target device configured to receive packets having the first format that conforms to the medical data protocol, wherein the second DPU is configured to process the one or more updated packets into the first format.

2. The system of claim 1, wherein to transform the one or more packets, the first DPU is to encrypt the one or more packets.

3. The system of claim 1, wherein to transform the one or more packets, the first DPU is to: select a compression technique from one or more compression techniques based at least in part on a criterion; and
compress the one or more packets utilizing the compression technique.

4. The system of claim 3, wherein the first DPU is to further:
identify a second compression technique associated with the one or more packets; and
compare the second compression technique with the one or more compression techniques, wherein the first DPU is to select the compression technique from the one or more compression techniques in response to the comparison.

5. The system of claim 3, wherein the first DPU is to further:
identify a type of data associated with the one or more packets, wherein the first DPU is to select the compression technique in response to identifying the type of data.

6. The system of claim 1, wherein the first DPU is to further:
receive a second set of packets for medical image data, the second set of packets having the first format that conforms to the medical data protocol;
process the second set of packets into a second set of updated packets having the first format that conforms to the medical data protocol, bypassing the kernel layer of the system; and
transmit the second set of updated packets to a first port of the target device, wherein the first DPU is to transmit the one or more updated packets to a second port of the target device.

7. The system of claim 1, wherein the protocol is a digital imaging and communications in medicine (DICOM) protocol.

8. A system comprising:
a first data processing unit (DPU) comprising dedicated hardware logic, the DPU configured to:

intercept one or more packets sent by a second DPU, the one or more packets having a first format that does not conform to a medical image data protocol before the one or more packets are received by a target device associated with a second format that conforms to the medical image data protocol;

transform, via the dedicated hardware logic of the DPU performing hardware-level packet transformation operations, bypassing a kernel layer of the system, the one or more packets to construct one or more updated packets having the second format that conforms to the medical imaging data protocol, wherein bypassing the kernel layer reduces latency compared to processing through the kernel layer; and transmit at least a portion of the one or more updated packets having the second format that conforms to the medical imaging data protocol to the target device.

9. The system of claim 8, wherein to construct the one or more updated packets, the first DPU is to decrypt the one or more packets received.

10. The system of claim 8, wherein to transform the one or more packets, the first DPU is to: identify a first portion of the one more updated packets associated with metadata; identify a second portion of the one or more updated packets associated with data; and transmit the first portion to the target device responsive to identifying the first portion.

11. The system of claim 10, wherein the first DPU is further to:

transmit the second portion directly to a first device, wherein the first device is a graphics processing unit (GPU), and wherein the second portion is not transmitted to the target device.

12. The system of claim 10, wherein the first DPU is further to:

compare the second portion with a threshold criterion;

determine the second portion satisfies the threshold criterion; and transmit the second portion to the target device responsive to determining the second portion satisfies the threshold criterion.

13. The system of claim 12, wherein the first DPU is further to:

store the one or more updated packets in a storage responsive to determining the second portion satisfies the threshold criterion.

14. The system of claim 12, wherein the first DPU is further to convert the second portion to a tensor before transmitting the second portion to a third device.

15. The system of claim 8, wherein the first DPU is configured to process the one or more packets at a component executing an application associated with the target device.

16. The system of claim 15, wherein:

the first DPU is configured to process the one or more packets at a first component executing an application; and the target device comprises a second component executing the application.

17. The system of claim 15, wherein the first DPU is further to:

filter the one or more packets at a second application, wherein the filtering is associated with pixel data of the one or more packets, and wherein the first DPU is to process the one or more updated packets at the first component in response to filtering the one or more packets.

18. The system of claim 15, wherein the first DPU is further to:

receive, from a server coupled with the first DPU, a request to initiate a remote direct memory access (RDMA) read;

read, from a picture archiving and communication system (PACS), data corresponding to the RDMA read in response to receiving the request; and store the data at a storage device coupled with the second DPU in response to reading the data.

19. A method, comprising:

receiving one or more packet, at a data processing unit (DPU) for medical imaging data, the DPU comprising dedicated hardware logic, the one or more packets having a first format that conforms to a medical imaging data protocol transforming, at the DPU via the dedicated hardware logic of the DPU performing hardware-level packet transformation operations, bypassing a kernel layer of the system associated with the DPU, the one or more packets into one or more updated packets having a second format that does not conform to the medical imaging data protocol, wherein bypassing the kernel layer reduces latency compared to processing through the kernel layer; and transmitting, by the first DPU, the one or more updated packets to a second DPU coupled to a target device configured to receive packets having the first format that conforms to the medical data protocol, wherein the second DPU is configured to process the one or more updated packets into the first format.

20. A method, comprising:

intercepting, at a first data processing unit (DPU) comprising dedicated hardware logic, one or more packets sent by a second DPU, the one or more packets having a first format that does not conform to a medical image data protocol before the one or more packets are received by a target device associated with second format that conforms to the medical image data protocol;

transforming, at the DPU via the dedicated hardware logic of the DPU performing hardware-level packet transformation operations, bypassing a kernel layer of a system associated with the DPU, the one or more packets to construct one or more updated packets having the second format that conforms to a medical imaging data protocol, bypassing a kernel layer of a system associated with the DPU, wherein bypassing the kernel layer reduces latency compared to processing through the kernel layer; and transmitting, by the DPU, at least a portion of the one or more updated packets having the second format that conforms to the medical imaging data protocol to the target device.

* * * * *